US009023002B2

United States Patent
Robinson et al.

(10) Patent No.: US 9,023,002 B2
(45) Date of Patent: May 5, 2015

(54) REDUCED-PRESSURE INTERFACES, SYSTEMS, AND METHODS EMPLOYING A COANDA DEVICE

(76) Inventors: Timothy Mark Robinson, Basingstoke (GB); Christopher Brian Locke, Bournemouth (GB)

(*) Notice: Subject to any disclaimer, the term of this patent is extended or adjusted under 35 U.S.C. 154(b) by 647 days.

(21) Appl. No.: 13/442,413

(22) Filed: Apr. 9, 2012

(65) Prior Publication Data
US 2013/0053796 A1  Feb. 28, 2013

Related U.S. Application Data

(60) Provisional application No. 61/529,751, filed on Aug. 31, 2011, provisional application No. 61/529,722, filed on Aug. 31, 2011, provisional application No. 61/529,709, filed on Aug. 31, 2011, provisional application No. 61/529,735, filed on Aug. 31, 2011.

(51) Int. Cl.
| A61M 1/00 | (2006.01) |
|---|---|
| A61F 13/02 | (2006.01) |
| A61M 27/00 | (2006.01) |
| A61M 5/178 | (2006.01) |
| A61M 5/00 | (2006.01) |
| A61M 5/32 | (2006.01) |
| A61M 35/00 | (2006.01) |
| A61F 13/00 | (2006.01) |

(52) U.S. Cl.
CPC ..... *A61F 13/00055* (2013.01); *Y10T 29/49826* (2015.01); *A61F 13/0216* (2013.01); *A61M 1/0058* (2013.01); *A61M 27/00* (2013.01); *A61M 1/009* (2014.02)

(58) Field of Classification Search
CPC ......... A61M 1/00; A61M 5/178; A61M 5/00; A61M 5/32; A61M 35/00; A61F 13/00
See application file for complete search history.

(56) References Cited

U.S. PATENT DOCUMENTS

| 1,355,846 A | 10/1920 | Rannells |
|---|---|---|
| 2,052,869 A * | 9/1936 | Coanda .................... 239/418 |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |

(Continued)

FOREIGN PATENT DOCUMENTS

| AU | 550575 A1 | 3/1986 |
|---|---|---|
| AU | 745271 | 4/1999 |

(Continued)

OTHER PUBLICATIONS

International Search Report for corresponding International Application No. PCT/US2012/032795 mailed Oct. 5, 2012.

(Continued)

*Primary Examiner* — Tatyana Zalukaeva
*Assistant Examiner* — Ilya Treyger

(57) ABSTRACT

Systems, devices, and methods for treating a wound on a patient involve a reduced-pressure interface having an interface body that facilitates the delivery of reduced pressure to the wound and also a Coanda device that develops an airflow over a wound dressing. The airflow developed by the Coanda device enhances evaporation of liquids from the dressing. Other systems, methods, and devices are presented herein.

20 Claims, 8 Drawing Sheets

(56) References Cited

U.S. PATENT DOCUMENTS

| | | |
|---|---|---|
| 2,969,057 A | 1/1961 | Simmons |
| 3,066,672 A | 12/1962 | Crosy, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0032762 A1 | 2/2007 | Vogel |
| 2010/0106079 A1* | 4/2010 | Alimi .............................. 604/24 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 0185248 A1 | 11/2001 |
| WO | 2005051461 A1 | 9/2005 |
| WO | 2009111657 A2 | 11/2009 |
| WO | WO 2011/130570 A1 * | 4/2011 |
| WO | 2011130570 A1 | 10/2011 |
| WO | 2012041296 A2 | 5/2012 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukie, Ž. Maksimovio, Đ. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

REDUCED-PRESSURE INTERFACES, SYSTEMS, AND METHODS EMPLOYING A COANDA DEVICE

RELATED APPLICATIONS

The present invention claims the benefit, under 35 USC §119(e), of the filings of U.S. Provisional Patent Application Ser. No. 61/529,751, entitled "REDUCED-PRESSURE INTERFACES, SYSTEMS, AND METHODS EMPLOYING A COANDA DEVICE," filed on 31 Aug. 2011, which is incorporated herein by reference for all purposes; U.S. Provisional Patent Application Ser. No. 61/529,722, entitled "REDUCED-PRESSURE DRESSINGS, SYSTEMS, AND METHODS WITH EVAPORATIVE DEVICES," filed on 31 Aug. 2011, which is incorporated herein by reference for all purposes; U.S. Provisional Patent Application Ser. No. 61/529,709, entitled "EVAPORATIVE FLUID POUCH AND SYSTEMS FOR USE WITH BODY FLUIDS," filed 31 Aug. 2011, which is incorporated herein by reference for all purposes; U.S. Provisional Patent Application Ser. No. 61/529,735, entitled "ABSORBENT POLYMER DRESSINGS, SYSTEMS, AND METHODS EMPLOYING EVAPORATIVE DEVICES," filed 31 Aug. 2011, which is incorporated herein by reference for all purposes; and U.S. patent application Ser. No. 13/084,813, entitled "DRESSINGS AND METHODS FOR TREATING A TISSUE SITE ON A PATIENT," filed on 12 Apr. 2011, which is incorporated herein by reference for all purposes.

TECHNICAL FIELD

The present disclosure relates generally to medical treatment systems, and more particularly, but not by way of limitation, to reduced-pressure interfaces, systems, and methods employing a Coanda device or other air-entrainment device.

BACKGROUND

Caring for wounds is important in the healing process. Wounds often produce considerable liquids, e.g., exudate. Medical dressings are frequently used in wound care to address the production of liquids from the wound. If not properly addressed, liquids at the wound can lead to infection or maceration of the periwound area. As used throughout this document, "or" does not require mutual exclusivity. Wound dressings may be used alone or as an aspect of applying reduced pressure to a tissue site.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

SUMMARY

According to an illustrative embodiment, a system for treating, a wound on a patient involves a reduced-pressure interface having an interface body that enables the delivery of reduced pressure to the wound and a Coanda device that develops an airflow over a wound dressing. The airflow developed by the Coanda device enhances evaporation of liquids from the dressing.

According to an illustrative embodiment, a system for treating a wound on a patient includes a wound-interface member and a sealing member for disposing over the wound interface member. The sealing member is formed with a treatment aperture. The system also includes a reduced-pressure interface coupled to the sealing member. The reduced-pressure interface includes an interface body comprising a conduit port, an access port, and a primary conduit. The primary conduit is in fluid communication with the conduit port and access port for transferring reduced pressure through the interface body. The reduced-pressure interface further comprises a base portion and a Coanda device associated with the interface body. The Coanda device is an aerodynamically shaped device that entrails or entrains airfow from the surrounding air through the presence of an area or greater positive pressure. There are various designs and shapes whereby this greater airflow may be entrained. These devices may also be referred to as Air-Multipliers.

The Coanda device includes an annular nozzle forming a central opening and includes an interior passage and a nozzle opening. The Coanda device includes a Coanda surface positioned proximate to and downstream from the nozzle opening. The Coanda device is positioned with a flow clearance from the base portion of the interface body, whereby fluid exiting the nozzle opening entrains additional fluid from the central opening and produces a combined fluid flow. The Coanda device is configured to direct the combined fluid flow to create a fluid flow over the sealing member. The system further includes a positive-pressure source fluidly coupled to the interior passage of the Coanda device for activating the Coanda device and includes a reduced-pressure source fluidly coupled to the conduit port for providing reduced pressure to the wound.

According to an illustrative embodiment, a reduced-pressure interface for providing reduced pressure to a tissue site and for delivering an airflow to an exterior of a dressing includes an interface body comprising a conduit port, an access port, and a primary conduit. The primary conduit is in fluid communication with the conduit port and access port for transferring reduced pressure through the interface body. The interface body also includes a base portion. The reduced-pressure interface further includes a Coanda device associated with the interface body. The Coanda device includes an annular nozzle forming a central opening and having an interior passage and a nozzle opening. The Coanda device also includes a Coanda surface positioned proximate to and downstream from the nozzle opening. The Coanda device is positioned with a flow clearance from the base portion of the interface body, whereby fluid exiting the nozzle opening entrains additional fluid from the central opening and produces a combined fluid flow. The Coanda device is configured to direct the combined fluid flow over the exterior of the dressing.

According to an illustrative embodiment, a method for treating a wound site on a patient includes disposing a wound-interface member proximate to the wound, covering the wound-interface member with a sealing member to create a sealed space, coupling a reduced-pressure interface to the sealing member, and fluidly coupling the reduced-pressure interface to the sealed space to deliver reduced pressure thereto. The reduced-pressure interface includes an interface body comprising a conduit port, an access port, and a primary conduit. The primary conduit is in fluid communication with the conduit port and access port for transferring reduced pressure through the interface body. The reduced-pressure interface further comprises a base portion. The reduced-pressure interface further includes a Coanda device associated with the interface body. The Coanda device includes an annular nozzle forming a central opening and having an interior passage and a nozzle opening. The Coanda device further includes a Coanda surface positioned proximate to and downstream from the nozzle opening. The Coanda device is positioned with a flow clearance from the base portion of the interface body, whereby fluid exiting the nozzle opening entrains additional fluid from the central opening and produces a combined fluid flow. The Coanda device is configured to direct the combined fluid flow to create a fluid flow over the sealing member. The method further includes providing reduced pressure to the conduit port of the reduced-pressure interface and providing positive pressure to the interior passage of the Coanda device to produce the combined fluid flow to generate a fluid flow over the sealing member.

According to an illustrative embodiment, a reduced-pressure interface for use in treating a wound on a patient includes an interface body having a conduit port, an access port, and a primary conduit. The primary conduit is in fluid communication with the conduit port and access port for transferring reduced pressure through the interface body. The interface body further includes a base portion and a neck portion. The reduced-pressure interface further includes a Coanda device disposed on the neck portion of the interface body. The Coanda device includes an annular nozzle forming a central opening and having an interior passage and a nozzle opening. The annular nozzle is positioned around the neck portion of the interface body. The Coanda device further includes a Coanda surface positioned proximate to and downstream from the nozzle opening, whereby fluid exiting the nozzle opening entrains additional fluid from the central opening and produces a combined fluid flow. The Coanda device is configured to direct the combined fluid towards the base portion of the interface body.

According to still an illustrative embodiment, a method of treating a wound on a patient includes disposing a wound-interface member proximate to the wound, covering the wound-interface member with a sealing member to create a sealed space, and coupling an interface body to the sealing member. The interface body includes a conduit port, an access port, and a primary conduit. The primary conduit is in fluid communication with the conduit port and access port for transferring reduced pressure through the interface body. The interface body further includes abase portion and a neck portion. The method further includes disposing a Coanda device around the neck portion of the interface body. The Coanda device includes an annular nozzle forming a central opening and having an interior passage and a nozzle opening. The annular nozzle is positioned around the neck portion. The Coanda device further includes a Coanda surface positioned proximate to and downstream from the nozzle opening, whereby fluid exiting the nozzle opening entrains additional fluid from the central opening and produces a combined fluid flow. The Coanda device is configured to direct the combined fluid towards the base portion of the interface body. The method further includes providing reduced pressure to the conduit port of the reduced-pressure interface and providing positive pressure to the interior passage of the Coanda device to produce the combined fluid flow that is directed toward the base portion of the interface body.

Other aspects, features, and advantages of the illustrative embodiments will become apparent with reference to the drawings and detailed description that follow.

DETAILED DESCRIPTION OF ILLUSTRATIVE EMBODIMENTS

Figure 1:
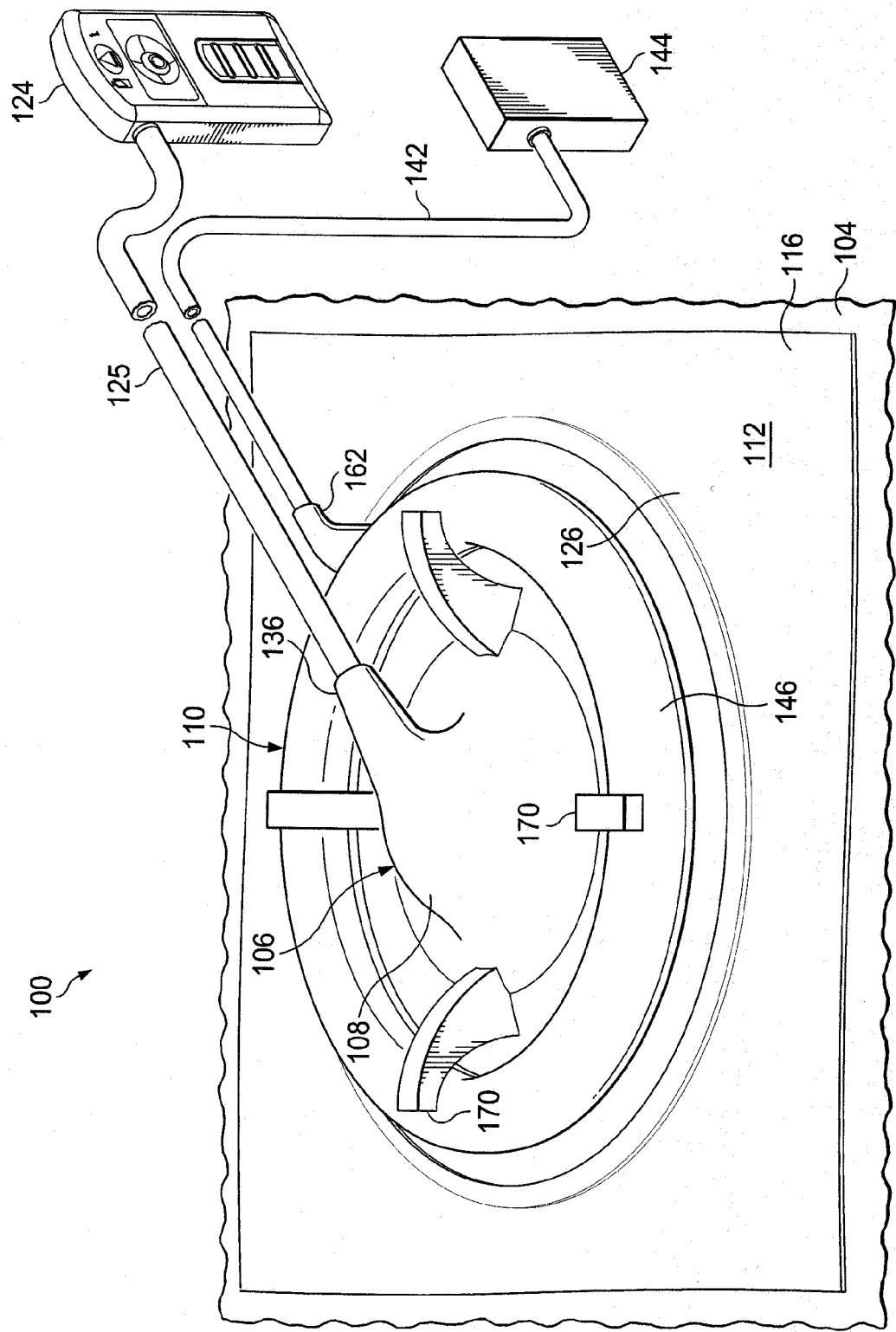
FIG. 1 is a schematic, perspective view of an illustrative embodiment of a system for treating a wound on a patient that includes a Coanda device.

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Referring to the figures and initially to FIG. 1-11, a system 100 for treating a wound 102 on a patient 104 is presented. The system 100 includes a reduced-pressure interface 106 that has an interface body 108 that enables the delivery of reduced pressure to the wound 102 and also a Coanda device 110 that develops an airflow over a wound dressing 112. The airflow developed by the Coanda device 110 enhances evaporation of liquids from the wound dressing 112 and among other things allows the wound dressing 112 to process relatively more fluids.

Figure 3:
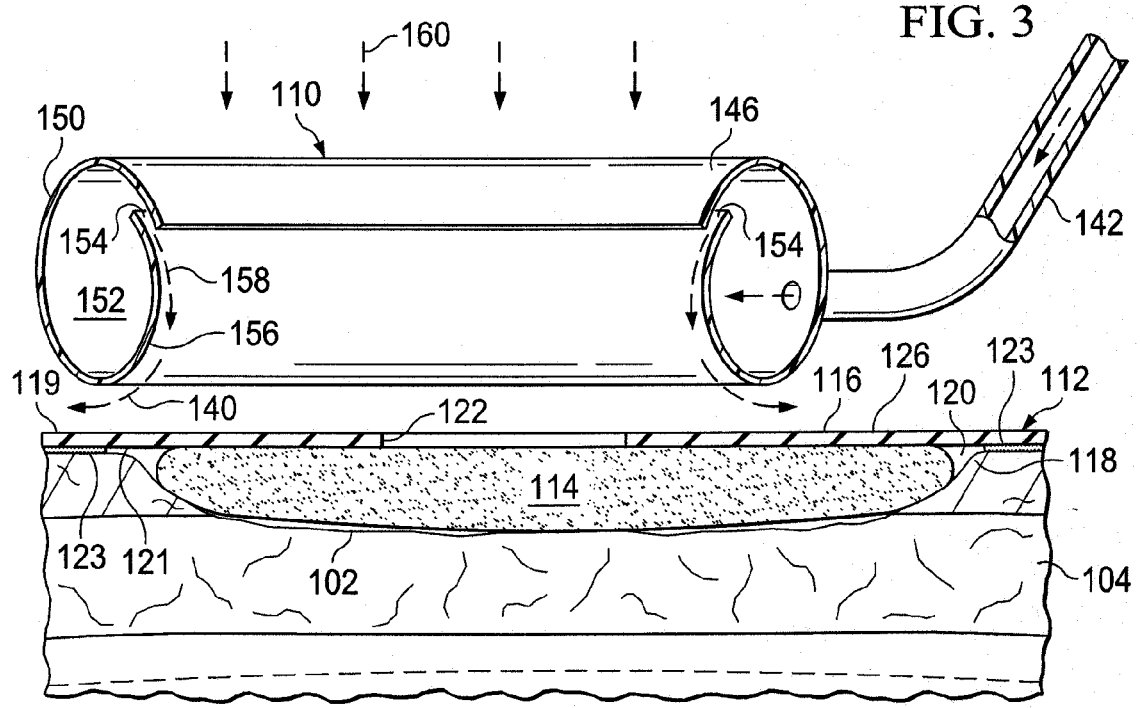
FIG. 3 is a schematic, perspective view, of the Coanda device of FIG. 2 shown over a wound.
Figure 4:
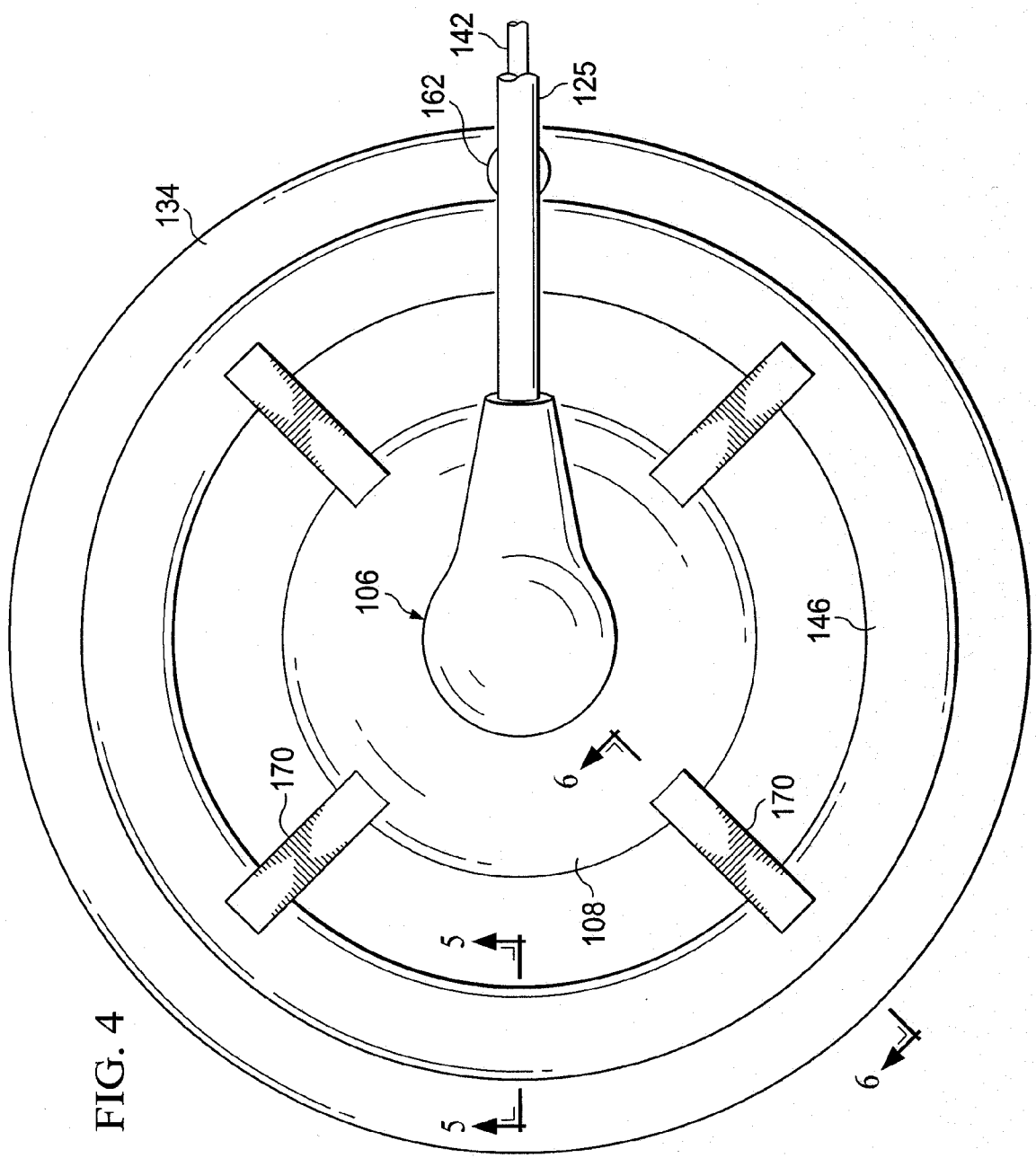
FIG. 4 is a schematic, plan view of an illustrative embodiment of a reduced-pressure interface that includes a Coanda device.
Figure 5:
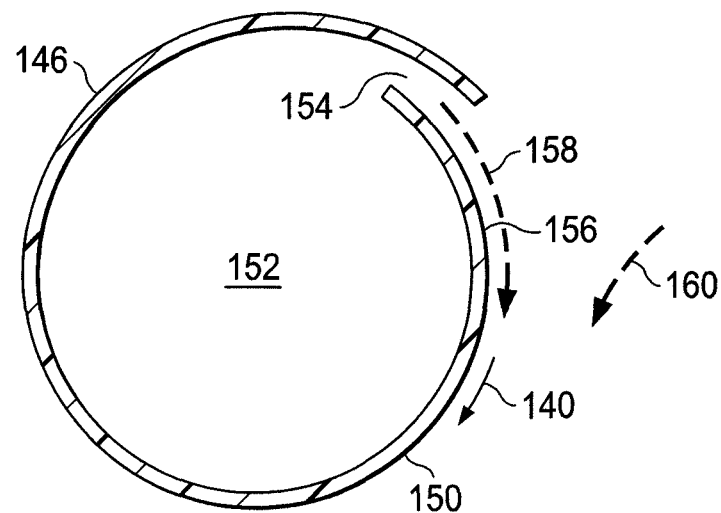
FIG. 5 is a schematic cross section of the Coanda device of the reduced-pressure interface of FIG. 4 taken along line 5-5.
Figure 6:
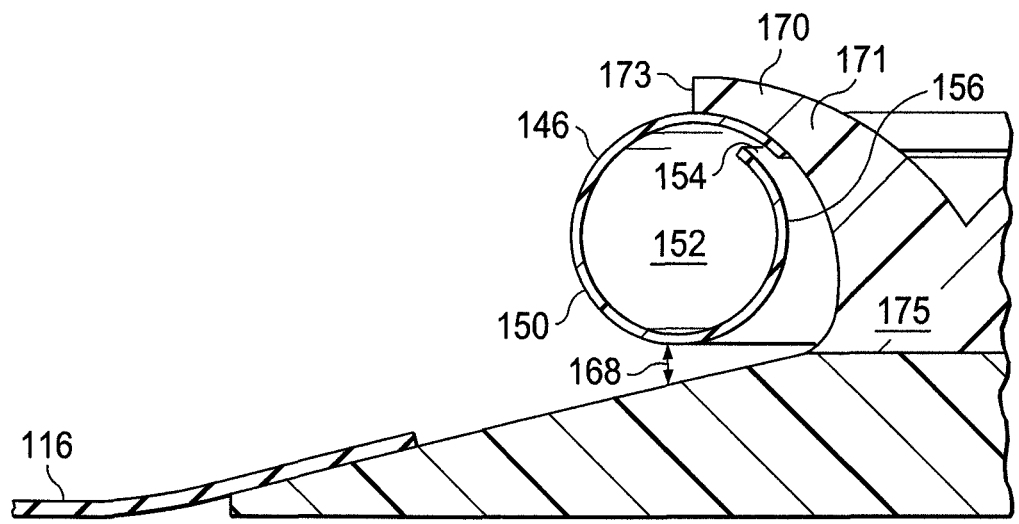
FIG. 6 is a schematic cross section of a portion of the reduced-pressure interface of FIG. 4 taken along line 6-6.

The system 100 may work with many types of dressings, but is shown in FIG. 3 with a wound dressing 112 that includes a wound-interface member 114 that is disposed proximate to the wound 102. The wound-interface member 114 may be a manifold or other material for interfacing with the wound 102. Manifold refers generally to a substance or structure that is provided to assist in applying reduced pressure to, delivering fluids to, or removing fluids from a tissue site, such as the wound 102. The manifold includes a plurality of flow channels or pathways that distribute fluids provided to and removed from the wound 102 around the manifold. In one illustrative embodiment, the flow channels or pathways are interconnected to improve distribution of fluids provided to or removed from the wound 102. The manifold may be a biocompatible material that is capable of being placed in contact with the wound 102 and distributing reduced pressure to the wound 102. Examples of manifolds include, without limitation, one or more of the following: devices that have structural elements arranged to form flow channels, such as, for example, cellular foam, open-cell foam, porous tissue collections, liquids, gels, and foams that include, or cure to include, flow channels; porous material porous, such as foam, gauze, felted mat, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material; or a scaffold material.

A sealing member 116 is disposed over the wound-interface member 114 and a portion of intact skin 118 to form a sealed space 120. A treatment aperture 122 is formed in the sealing member 116 to provide fluid access to the sealed space 120. The reduced-pressure interface 106 (not shown in FIG. 3) is in fluid communication with the treatment aperture 122. A plurality of turbulence generators 117 (FIG. 10) may be formed on the first side 126 of the wound dressing 112, or more specifically a first side 119 of the sealing member 116. The turbulence generators 117 may be notches, nodules, shaped extensions on the first side 126 of the sealing member 116 that encourage the air flow to become turbulent.

The sealing member 116 may be any liquid-impervious material that forms the sealed space 120 into which reduced pressure is applied. The sealing member 116 may be formed from a high-moisture-vapor-transfer-rate material (high MVTR material) or a drape material. "Moisture Vapor Transmission Rate" or "MVTR" represents the amount of moisture that can pass through a material in a given period of time. A high-moisture-vapor-transfer-rate material typically has a moisture vapor transmission rate greater than 300 g/m$^2$/24 hours and more typically 1000 g/m$^2$/24 hours or more. The sealing member 116 allows vapor to egress from the sealed space 120 through sealing member 116 to the atmosphere. The Coanda device 110 moves air across the first side 119 of the sealing member 116 and thereby creates an enhanced or strong relative humidity gradient.

The sealing member 116 may comprise one or more of the following: hydrophilic polyurethane, cellulosics, hydrophilic polyamides, an INSPIRE 2301 material from Expopack Advanced Coatings of Wrexham, United Kingdom; a thin, uncoated polymer drape, natural rubbers, polyisoprene, styrene butadiene rubber, chloroprene rubber, polybutadiene, nitrite rubber, butyl rubber, ethylene propylene rubber, ethylene propylene diene monomer, chlorosulfonated polyethylene, polysulfide rubber, polyurethane (PU), EVA film, copolyester, silicones, silicone drape, a 3M Tegaderm® drape, or a polyurethane (PU) drape such as one available from Avery Dennison Corporation of Pasadena, Calif., polyether block polyamide copolymer (PEBAX) for example from Arkema, France, or other appropriate material.

An attachment device 123, e.g., an adhesive, is coupled to all or a portion of a second, patient-facing side 121 of the sealing member 116. The attachment device 123 attaches the sealing member 116 to a portion of intact skin 118 of the patient or a portion of the wound-interface member 114.

As previously noted, the sealing member 116 may be adhered to the intact skin 118 by the attachment device 123, e.g., an adhesive, or to the wound-interface member 114. The performance of the sealing member 116 with respect to MVTR may be enhanced by only covering a limited surface area of the second, patient-facing side 121 of the sealing member 116 with the attachment device 123. For example, only the peripheral edge of the sealing member 116 may be covered or a limited pattern may be used. In the latter situation, according to one illustrative embodiment, only 30 to 60 percent of the surface area is covered with the attachment device 123. The limited coverage by the attachment device 123 on the second, patient-facing side 121 may be accomplished by applying the attachment device 123 in a pattern, e.g., grid, spaced dots, swirls, or other patterns. In another embodiment, the sealing member 116 may be coupled by welding (e.g., ultrasonic or RF welding), bonding, stitching, staples, or another coupling device to the first side 114 of the wound-interface member 114. The attachment device 123 may be applied only to a peripheral portion of the sealing member 116.

The reduced-pressure interface 106 functions to accomplish two tasks. First, the reduced-pressure interface 106 receives reduced pressure from a reduced-pressure source 124 and produces an airflow across the first side 126 of the wound dressing 112, or more particularly the first side 119 of the sealing member 116. The reduced-pressure interface 106 includes the interface body 108 and the Coanda device 110 that may be associated with one another in a several ways: coupled, formed integrally, or placed adjacent to one another. The reduced-pressure interface 106 is coupled to the first side 126 of the sealing member 116.

It should be noted in other embodiments other entrainment devices may be used as the Coanda device 110 to entrain air and direct the air over the wound dressing 112 to achieve the desired air-flow. These other devices may be used to entrain air to create a more voluminous flow due to the presence of a high pressure flow, such as a Conventional Ejector, where a primary flow is located proximate to an available secondary air source that is "dragged" by an aerofoil shape to have the effect of an air-multiplier.

The reduced-pressure source 124 may be any device for supplying a reduced pressure, such as a vacuum pump, wall suction, micro-pump, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). If a separate unit as shown in FIG. 1, the reduced-pressure source 124 is fluidly coupled to the reduced-pressure interface 106 by a reduced-pressure conduit 125.

Figure 7:
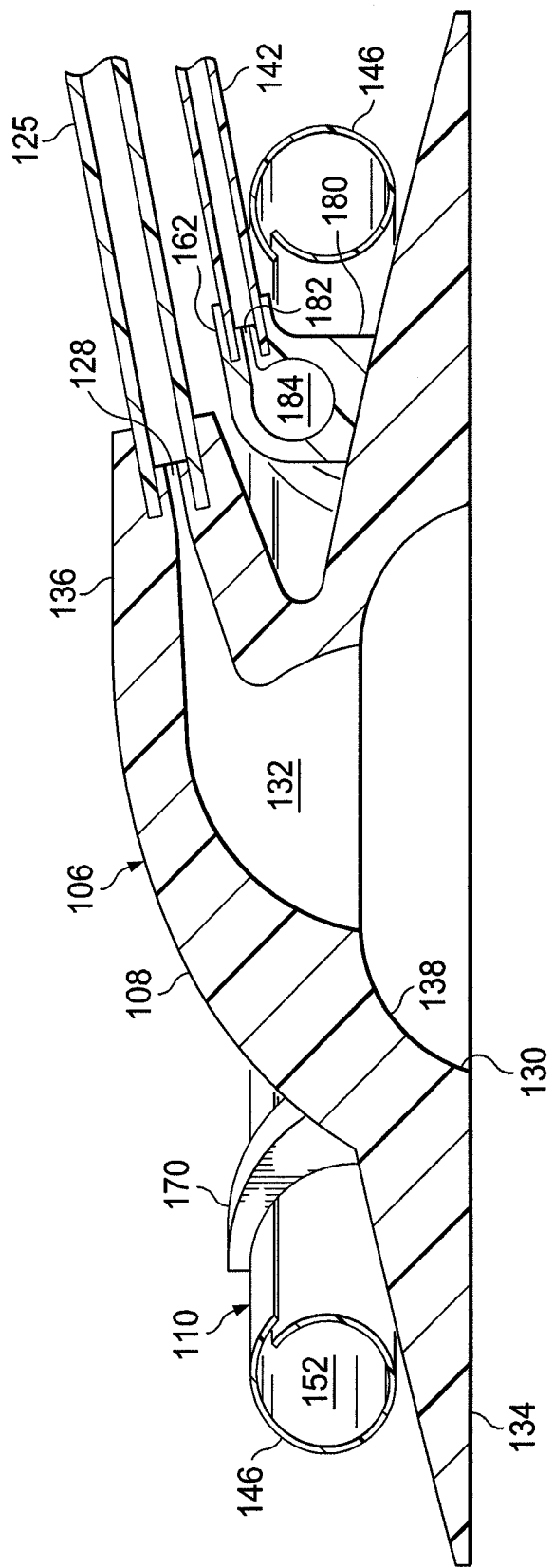
FIG. 7 is a schematic cross section of an illustrative embodiment of a reduced-pressure interface.

The reduced-pressure interface 106 includes the interface body 108. Referring now primarily to FIG. 7, the interface body 108 includes a conduit port 128, an access port 130, and a primary conduit 132. The primary conduit 132 is in fluid communication with the conduit port 128 and access port 130 for transferring reduced pressure through the interface body 108. The reduced-pressure interface further includes a base portion 134 and may include a neck portion 136. The access port 130 may also include a recess or recessed portion 138. The interface body 108 may be formed from an medically-acceptable polymer, e.g., polyurethane, plasticized PVC, thermoplastic elastomer (TPE), PEBAX, and silicone polymers.

As previously mentioned, the reduced-pressure interface 106 includes the Coanda device 110. The Coanda device 110 is a device for entraining air for desired purpose using the Coanda effect. The Coanda effect is generally phenomena in which a flow attaches itself to a nearby surface and remains attached even as the surface (Coanda surface) pulls away from the flows initial direction. As the flow curves away, the flow will entrain surrounding fluids and increase the volume of the flow. Without being limited to theory, it appears that the surface that is brought close to the flow restricts the entrainment in that region and as the flow accelerates to try to balance the momentum transfer, a pressure differential develops across the flow and the direction is changed or deflected closer to the surface. The effect is named for Henri Coanda and the concept is described in U.S. Pat. No. 2,052,869, granted to Coanda.

Figure 2:
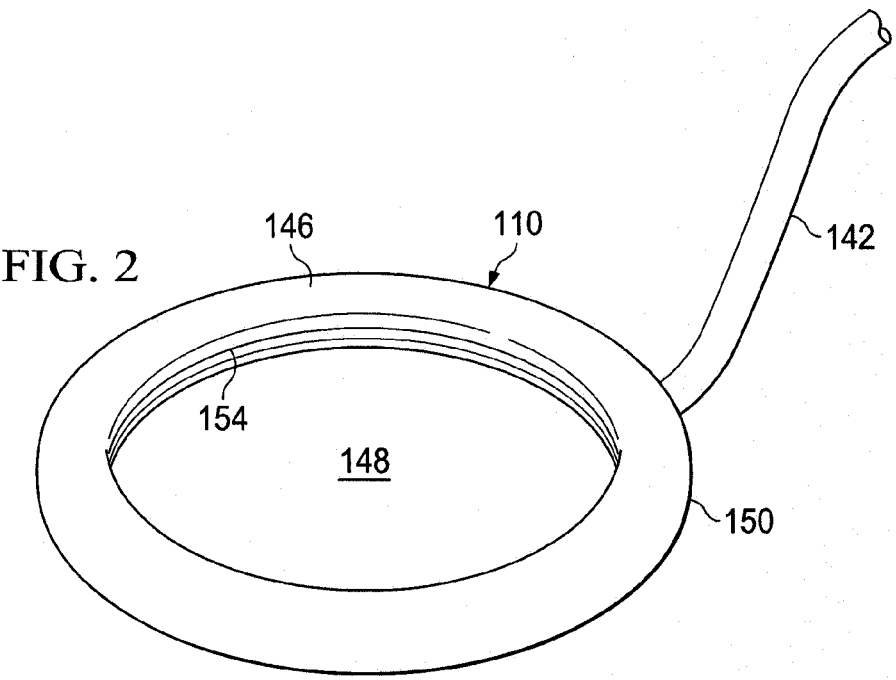
FIG. 2 is a schematic, perspective view of an illustrative embodiment of a Coanda device.

Thus, as shown well in FIGS. 2 and 3, the Coanda device 110 creates a desired airflow as suggested by arrows 140. The Coanda device 110 is fluidly coupled by a conduit 142 to a positive-pressure source 144, which supplies relatively high pressure air. As used herein, air is intended to cover other working gases that may be used to help remove moisture. The Coanda device 110 receives positive pressure air from the conduit 142 and develops an enhanced air low that is delivered from the Coanda device 110 over the first side 126 of the wound dressing 112. As the air moves across the wound dressing 112, any moisture or vapor on the first side 126 of the sealing member 116 is moved. This in turn will increase or maintain a strong relative humidity gradient across the sealing member 116 that helps remove liquid from the wound dressing 112. That in turn may provide many benefits including an increased ability to process liquids.

The Coanda device 110 includes an annular nozzle 146. The annular nozzle 146 forms a central opening 148. The central opening 148 surrounds much of the interface body 108 and a portion of the interface body 108 extends through the central opening 148. The annular nozzle 146 has walls 150 that form an interior passage 152. A nozzle opening 154 is formed on the annular nozzle 146 on a portion in or near the central opening 148. A portion of the walls 150 forms a Coanda surface 156 proximate to and downstream from the nozzle opening 154. The fluid or air exiting the nozzle opening 154 entrains additional fluid from the central opening 148 as the air flow follows the Coanda surface 156. The flow of air from the nozzle opening 154 plus the entrained air from the central opening 148 produces a combined fluid flow.

For the configuration shown, air is moved out of the nozzle opening 154 as suggested by arrows 158 in FIG. 3. The airflow entrains additional air from the central opening 148 as suggested by arrows 160. The combined fluid flow is suggested by arrows 140. It should be apparent that if a volume $V_1$ of air is delivered by conduit 142 to the Coanda device 110 over a time T and a volume $V_2$ of air is delivered through the central opening 148 of the Coanda device 110 over time T, the combined air flow $(V_2+V_1)$ will be enhanced or more volumuous than the original supply $(V_1)$. It should be understood that the Coanda device 110 may be flipped, or rotated, such that the nozzle opening 154 discharges air away from base portion 134 of the interface body 108 and air that is recruited from the central opening 148 is pulled from proximate the first side 119 of the sealing member 116.

The positive-pressure source 144 is fluidly coupled to the interior passage 152 of the Coanda device 110. The conduit 142 fluidly may fluidly couple the positive-pressure source 144 to a pressure coupling 162. The pressure coupling 162 may be separate from the interface body 108 as shown in FIG. 1 or integrated as part of the interface body 108 as shown in FIG. 7.

Figure 9:
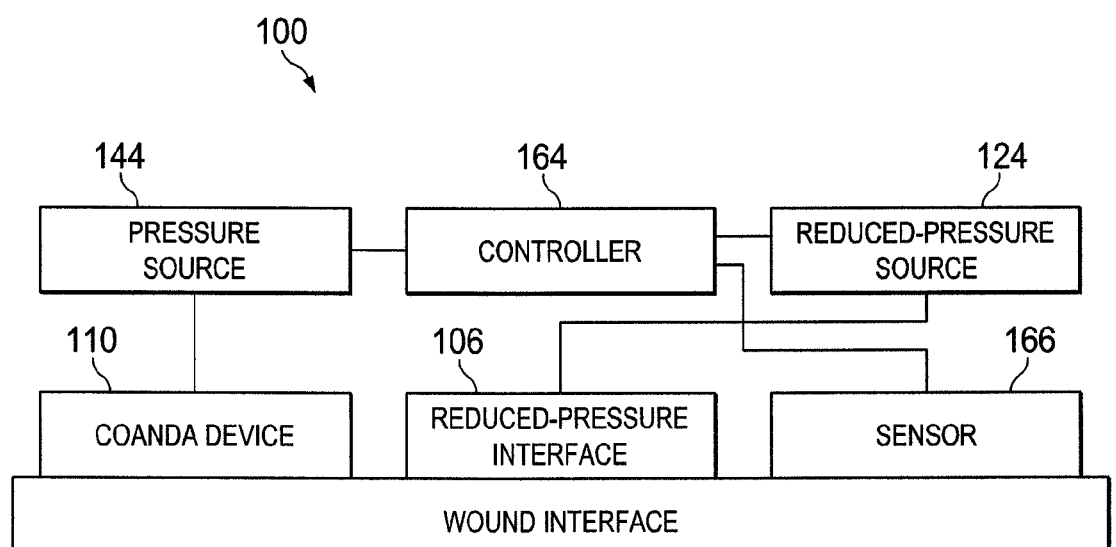
FIG. 9 is a schematic diagram of an illustrative embodiment of a system for treating a wound on a patient that includes active control.
Figure 10:
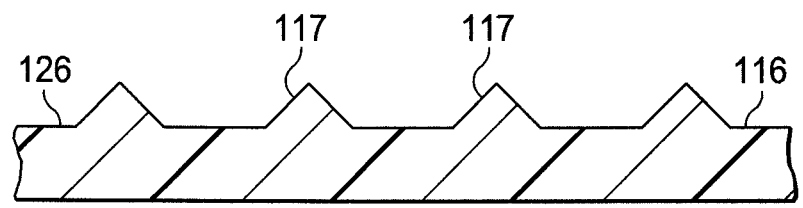
FIG. 10 is a schematic cross section of a portion of a sealing member that includes an illustrative embodiment of a plurality of turbulence generators.

The positive-pressure source 144 may be activated continuously or intermittently. The positive-pressure source 144 may also be actively controlled. Referring now primarily to FIG. 9, if actively controlled, the system 100 further includes a controller 164 and a saturation sensor 166 operatively coupled to the wound-interface member 114 and the controller 164. The saturation sensor 166 may be any device that allows monitoring of the saturation of the wound-interface member 114. For example, without limitation, the saturation sensor 166 may be a resistive element that changes resistance when liquid covers the resistive elements, a galvanic cell that creates a voltage when covered with liquid from a wound, capacitive sensor in which the capacitance changes when liquid is in the area of the sensor, an optical sensor that is sensitive to the change in light transmission as the sensor is covered with liquid, or a sound sensor that measures the change in sound frequency or loudness as liquid covers the sensor, or other device.

The controller 164 and saturation sensor 166 are operative to determine when the wound-interface member 114 is saturated. The controller 164 is operatively coupled to the positive-pressure source 144. The controller 164 activates the positive-pressure source 144 when the controller 164 and saturation sensor 166 determine the wound-interface member 114 is saturated. Likewise, the system 100 may be further configured such that the controller 164 deactivates the positive-pressure source 144 when the controller 164 and saturation sensor 166 determine that the wound-interface member 114 is no longer saturated or after a timed period.

A number of devices or elements may be used to position the Coanda device 110 to have a flow clearance 168 between the Coanda device 110 and the base portion 134 of the interface body 108. For example, as seen clearly in FIGS. 1, 4, 6, and 7, a plurality of rib members 170 may be used to suspend the annular nozzle 146 of the Coanda device 110 to create the flow clearance 168. One or more of the rib members 170 may have a pressure conduit in an interior portion that is in fluid communication with the interior passage 152 of the Coanda device 110 and the positive-pressure source 144. Each rib member 170 has an arm 171 with a distal portion 173 attached to a portion of the annular nozzle 146 and proximal portion 175 attached to the interface body 108. The coupling at the distal portion 173 with the annular nozzle 146 may be by welding, bonding, adhesives, cements, stitching, staples, or other coupling device.

Figure 11:
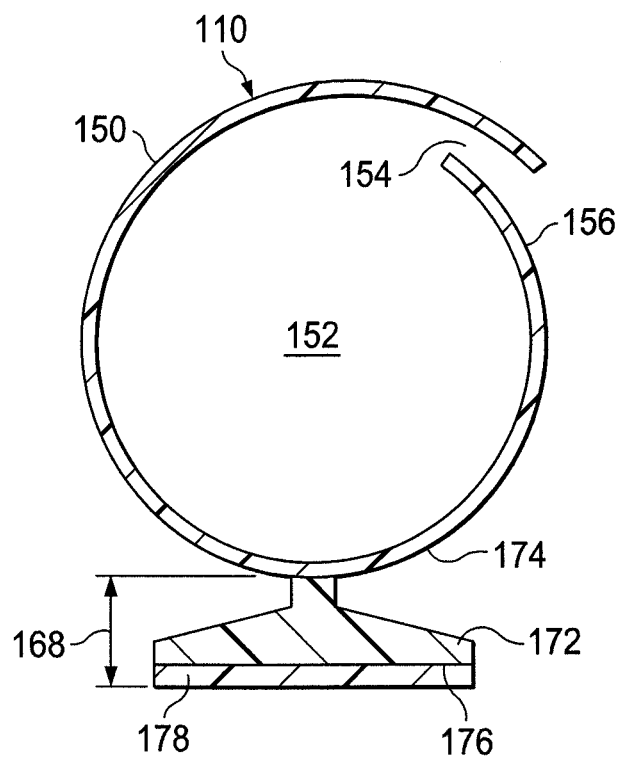
FIG. 11 is a schematic cross section of the Coanda device with a plurality of base stands.

In another approach, as shown in FIG. 11, a plurality of base stands 172 may be attached to a bottom portion 174 of the annular nozzle 146. In one embodiment, the plurality of base stands 172 are attached to the bottom portion 174 of the annular nozzle 146 and each base stand has a base 176 with an adhesive 178 for attaching the Coanda device 110 to the base portion 134 of the interface body 108. In this way, the Coanda device 110 may be added to an existing reduced-pressure interface.

Figure 8:
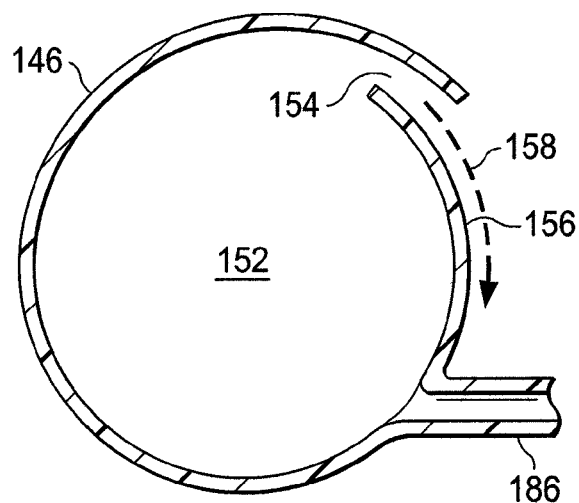
FIG. 8 is a schematic cross section of another portion of the illustrative embodiment of the reduced-pressure interface of FIG. 7.

Referring now primarily to FIGS. 7-8, the reduce-pressure interface 106 has some variation from other illustrative embodiments presented. In particular, a positive-pressure housing 180 has been added for the pressure coupling 162. The positive-pressure housing 180 has an entry port 182, a main conduit 184, and a delivery port 186. The delivery port 186 delivers the air to the interior passage 152.

According to one illustrative embodiment, in operation, the wound 102 is treated by disposing the wound-interface member 114 proximate to the wound 102 and covering the wound-interface member 114 with the sealing member 116 to create the sealed space 120. The reduced-pressure interface 106 is coupled to the sealing member 116. The reduced-pressure interface 106 is fluidly coupled to the sealed space 120 to deliver reduced pressure to the sealed space 120. The fluid coupling is typically accomplished by coupling a reduced-pressure conduit 125 to the conduit port 128 of the reduced-pressure interface 106. Reduced pressure is delivered to the conduit port 128 to provide reduced pressure to the wound 102. To help process liquid removed from the wound 102 and held in the wound-interface member 114 or another part of the wound dressing 112, positive pressure is provided to the interior passage 152 of the Coanda device 110 to produce the combined fluid flow that generates a fluid flow over the sealing member 116 of the wound dressing 112.

Treatment of the wound 102 in this way may involve continuous air flow, intermittent air flow, or active control of the positive-pressure source 144. In the latter situation, when the controller 164 and saturation sensor 166 determine that the wound-interface member 114 is saturated, the controller 164 activates the positive-pressure source 144. In addition, the controller 164 may stop the flow when the controller 164 and saturation sensor 166 determine that the wound-interface member 114 is no longer saturated.

Figure 12:
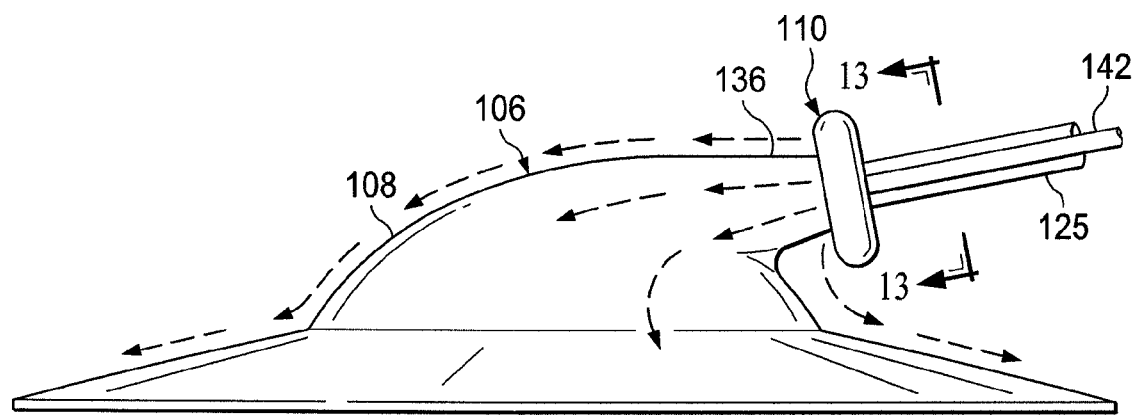
FIG. 12 is a schematic, elevation view of an illustrative embodiment of a reduced-pressure interface that includes a Coanda device.
Figure 13:
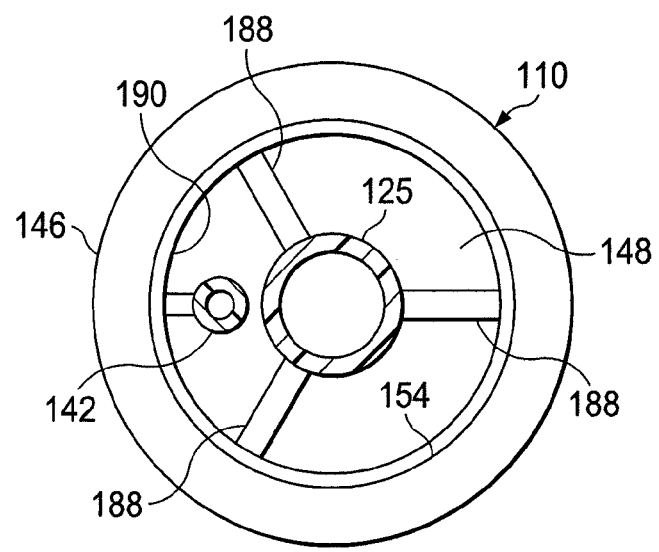
FIG. 13 is a cross section taken along line 13-13 in FIG. 12.

Referring now primarily to FIGS. 12 and 13, another illustrative embodiment of a reduced-pressure interface 106 is presented. The reduced-pressure interface 106 is analogous in many respects to the reduced-pressure interface 106 of FIGS. 1-11, and accordingly, some parts are labeled but not further discussed. The reduced-pressure interface 106 of FIGS. 12-13 primarily differs in that the Coanda device 110 is sized, configured, and positioned to be on the neck portion 136 of the interface body 108 or the reduced-pressure conduit 125. The Coanda device 110 moves air from that position towards the base portion 134 of the interface body 108. The inside diameter of the central opening 148 may be sized to be 110 to 200 percent of the outside diameter of the neck portion 136 of the interface body 108.

As shown best in FIG. 13, a plurality of leg members 188 may be coupled to annular nozzle 146 on an interior portion 190. The plurality of leg members 188 maintain a clearance between the annular nozzle 146 and the neck portion 136 of the interface body 108.

The reduced-pressure interface 106 of FIGS. 12-13 is used in the same manner as the previously presented embodiments, except a step involves disposing the Coanda device 110 on the neck portion 136 of the interface body 108. This design allows a user to add the Coanda device 110 to an existing reduced-pressure interface at the time of use The illustrative embodiments herein offer a number of perceived advantages. For example, one or more embodiments herein may be used with existing systems or interfaces. The embodiments herein increase the quantity of liquid that may be processed by a wound dressing. No additional or minimal training is required to use the embodiments. If the reduce-pressure interface fails with respect to the Coanda device 110, the consequences do not pose a significant risk to the patient. These are only a few possible advantages.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. For example, without limitation, the control components of FIG. 9 may added to any of the embodiments herein, such as the reduced-pressure interface of FIG. 12.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a wound on a patient, the system comprising:
    a wound-interface member;
    a sealing member for disposing over the wound interface member, wherein the sealing member is formed with a treatment aperture;
    a reduced-pressure interface coupled to the sealing member, wherein the reduced-pressure interface comprises:
        an interface body comprising a conduit port, an access port, and a primary conduit, wherein the primary conduit is in fluid communication with the conduit port and access port for transferring reduced pressure through the interface body and further comprising a base portion, and
        a Coanda device associated with the interface body, wherein the Coanda device comprises:
            an annular nozzle forming a central opening and having an interior passage and a nozzle opening,
            a Coanda surface positioned proximate to and downstream from the nozzle opening,
            wherein the Coanda device is positioned with a flow clearance from the base portion of the interface body, whereby fluid exiting the nozzle opening entrains additional fluid from the central opening and produces a combined fluid flow, and
            wherein the Coanda device is configured to direct the combined fluid flow to create a fluid flow over the sealing member; and
    a positive-pressure source fluidly coupled to the interior passage of the Coanda device for activating the Coanda device; and
    a reduced-pressure source fluidly coupled to conduit port for providing reduced pressure to the wound.

2. The wound treatment system of claim 1, wherein the wound treatment system further comprises:
    a controller;
    a saturation sensor operatively coupled to the wound-interface member and the controller;
    wherein the controller and saturation sensor are operative to determine when the wound-interface member is saturated;

wherein the controller is operatively coupled to the positive-pressure source and wherein the controller activates the positive-pressure source when the controller and saturation sensor determine the wound-interface member is saturated.

3. The wound treatment system of claim 2, wherein the controller deactivates the positive-pressure source when the controller and saturation sensor determine that the wound-interface is no longer saturated.

4. The wound treatment system of claim 1, wherein the sealing member has a first side and a second, patient-facing side and further comprising a plurality of turbulence generators on the first side of the sealing member.

5. The wound treatment system of claim 1, wherein the positive-pressure source is fluidly coupled to the interior passage of the Coanda device by a rib member having a pressure conduit in fluid communication with the interior passage and the positive-pressure source.

6. The wound treatment system of claim 1, wherein the Coanda device is configured to direct the combined fluid flow directly onto the sealing member.

7. The wound treatment system of claim 1, wherein the Coanda device is configured to direct the combined fluid flow into the central opening and thereby pull air across the sealing member through the flow clearance and into the central opening.

8. The wound treatment system of claim 1, wherein the Coanda device further comprises a plurality of base stands coupled to the base portion and creating the flow clearance and wherein the Coanda device is associated with the interface body by the plurality of base stands.

9. The wound treatment system of claim 1, wherein the access port includes a recessed portion.

10. The wound treatment system of claim 2, wherein the controller deactivates the positive pressure source when the controller and saturation sensor determine that the wound-interface is substantially unsaturated.

11. A reduced-pressure interface for providing reduced pressure to a tissue site and for delivering an airflow to an exterior of a dressing, the reduced-pressure interface comprising:
an interface body comprising a conduit port, an access port, and a primary conduit, wherein the primary conduit is in fluid communication with the conduit port and access port for transferring reduced pressure through the interface body, and further comprising a base portion; and
and a Coanda device associated with the interface body, wherein the Coanda device comprises:
an annular nozzle forming a central opening and having an interior passage and a nozzle opening,
a Coanda surface positioned proximate to and downstream from the nozzle opening,
wherein the Coanda device is positioned with a flow clearance from the base portion of the interface body, whereby fluid exiting the nozzle opening entrains additional fluid from the central opening and produces a combined fluid flow, and
wherein the Coanda device is configured to direct the combined fluid flow over the exterior of the dressing.

12. The reduced-pressure interface of claim 11, further comprising a plurality of base stands coupled to the base portion of the interface body for creating the flow clearance and for associating the Coanda device with the interface body.

13. A reduced-pressure interface for use in treating a wound on a patient, the reduced-pressure interface comprising:
an interface body comprising a conduit port, an access port, and a primary conduit, wherein the primary conduit is in fluid communication with the conduit port and access port for transferring reduced pressure through the interface body, and further comprising a base portion and a neck portion; and
and a Coanda device disposed on the neck portion of the interface body, wherein the Coanda device comprises:
an annular nozzle forming a central opening and having an interior passage and a nozzle opening, wherein the annular nozzle is positioned around the neck portion,
a Coanda surface positioned proximate to and downstream from the nozzle opening, whereby fluid exiting the nozzle opening entrains additional fluid from the central opening and produces a combined fluid flow, and
wherein the Coanda device is configured to direct the combined fluid towards the base portion of the interface body.

14. The reduced-pressure interface of claim 13, wherein the Coanda device further comprises a plurality of leg members coupled to annular nozzle for maintaining a clearance between the annular nozzle and the neck portion of the interface body.

15. A method of treating a wound on a patient, the method comprising:
disposing a wound-interface member proximate to the wound;
covering the wound-interface member with a sealing member to create a sealed space;
coupling an interface body to the sealing member, wherein the interface body comprises a conduit port, an access port, and a primary conduit, wherein the primary conduit is in fluid communication with the conduit port and access port for transferring reduced pressure through the interface body, and wherein the interface body further comprises a base portion and a neck portion;
disposing a Coanda device around the neck portion of the interface body, wherein the Coanda device comprises:
an annular nozzle forming a central opening and having an interior passage and a nozzle opening, wherein the annular nozzle is positioned around the neck portion,
a Coanda surface positioned proximate to and downstream from the nozzle opening, whereby fluid exiting the nozzle opening entrains additional fluid from the central opening and produces a combined fluid flow, and
wherein the Coanda device is configured to direct the combined fluid towards the base portion of the interface body; and
providing reduced pressure to the conduit port of the reduced-pressure interface; and
providing positive pressure to the interior passage of the Coanda device to produce the combined fluid flow that is directed toward the base portion of the interface body.

16. The method of claim 15, further comprising operatively coupling a saturation sensor to the wound-interface member and to a controller; and when the controller and saturation sensor determine that the wound-interface member is saturated, activating the positive-pressure source.

17. The method of claim 16, further comprising deactivating the positive-pressure source when the controller and saturation sensor determine that the wound-interface member is no longer saturated.

18. A method for treating a wound site on a patient, the method comprising:

disposing a wound-interface member proximate to the wound;
covering the wound-interface member with a sealing member to create a sealed space;
coupling a reduced-pressure interface to the sealing member and fluidly coupling the reduced-pressure interface to the sealed space to deliver reduced pressure thereto, wherein the reduced-pressure interface comprises:
an interface body comprising a conduit port, an access port, and a primary conduit, wherein the primary conduit is in fluid communication with the conduit port and access port for transferring reduced pressure through the interface body, and further comprising a base portion,
and a Coanda device associated with the interface body, wherein the Coanda device comprises:
an annular nozzle forming a central opening and having an interior passage and a nozzle opening,
a Coanda surface positioned proximate to and downstream from the nozzle opening,
wherein the Coanda device is positioned with a flow clearance from the base portion of the interface body, whereby fluid exiting the nozzle opening entrains additional fluid from the central opening and produces a combined fluid flow, and
wherein the Coanda device is configured to direct the combined fluid flow to create a fluid flow over the sealing member;
providing reduced pressure to the conduit port of the reduced-pressure interface; and
providing positive pressure to the interior passage of the Coanda device to produce the combined fluid flow to generate a fluid flow over the sealing member.

19. The method of claim 18, further comprising operatively coupling a saturation sensor to the wound-interface member and to a controller; and when the controller and saturation sensor determine when the wound-interface member is saturated and then activates the positive-pressure source.

20. The method of claim 18, further comprising deactivating the positive-pressure source when the controller and saturation sensor determine that the wound-interface member is no longer saturated.

* * * * *